(12) United States Patent
Bazer-Bachi et al.

(10) Patent No.: US 10,744,489 B2
(45) Date of Patent: Aug. 18, 2020

(54) METHOD FOR PREPARING SOLIDS FROM A MIXTURE OF AT LEAST TWO MALACHITE POWDERS

(71) Applicants: AXENS, Rueil Malmaison (FR); IFP Energies nouvelles, Rueil-Malmaison (FR)

(72) Inventors: Delphine Bazer-Bachi, Saint Privat des Vieux (FR); David Chiche, Lyons (FR); Joseph Lopez, Saint Julien les Rosiers (FR); Thomas Serres, Langlade (FR); Tom Frising, Nanterre (FR); Olivier Ducreux, Louveciennes (FR); Patrick Euzen, Paris (FR)

(73) Assignees: AXENS, Rueil, Malmaison (FR); IFP Energies nouvelles, Rueil-Malmaison (FR)

( * ) Notice: Subject to any disclaimer, the term of this patent is extended or adjusted under 35 U.S.C. 154(b) by 101 days.

(21) Appl. No.: 16/006,065

(22) Filed: Jun. 12, 2018

(65) Prior Publication Data

US 2018/0353941 A1 Dec. 13, 2018

(30) Foreign Application Priority Data

Jun. 13, 2017 (FR) .................................... 17 55303

(51) Int. Cl.
*B01J 23/72* (2006.01)
*B01J 21/16* (2006.01)
(Continued)

(52) U.S. Cl.
CPC .............. *B01J 23/72* (2013.01); *B01D 15/08* (2013.01); *B01D 53/02* (2013.01); *B01D 53/04* (2013.01);
(Continued)

(58) Field of Classification Search
CPC . B01J 21/16; B01J 23/72; B01J 35/002; B01J 37/0009; B01J 37/0018; B01J 37/04; B01J 37/088
See application file for complete search history.

(56) References Cited

U.S. PATENT DOCUMENTS 3,647,423 A * 3/1972 Acoveno ............. C22B 15/0078
75/365
3,988,263 A 10/1976 Hansford
(Continued)

FOREIGN PATENT DOCUMENTS

EP 2591842 B1 6/2018
WO 1995024962 A1 9/1995

OTHER PUBLICATIONS

Search Report in corresponding EP appl. No. 1755303 dated Feb. 7, 2018.
(Continued)

*Primary Examiner* — Cam N. Nguyen
(74) *Attorney, Agent, or Firm* — Millen White Zelano and Branigan, PC; John Sopp

(57) ABSTRACT

The invention relates to a method for preparing a solid comprising a step of mixing a set of compounds comprising at least two $Cu_2(OH)_2CO_3$ powders of different particle sizes and at least one binder and the use of the solid prepared by means of this method.

11 Claims, 1 Drawing Sheet

(51) Int. Cl.
| | |
|---|---|
| B01J 35/00 | (2006.01) |
| B01J 37/00 | (2006.01) |
| B01J 37/04 | (2006.01) |
| B01J 37/08 | (2006.01) |
| C10L 3/10 | (2006.01) |
| C10G 25/00 | (2006.01) |
| C01B 3/16 | (2006.01) |
| B01D 15/08 | (2006.01) |
| B01D 53/02 | (2006.01) |
| C07C 29/154 | (2006.01) |
| C04B 35/632 | (2006.01) |
| B01D 53/04 | (2006.01) |
| C04B 35/45 | (2006.01) |
| B01D 53/48 | (2006.01) |
| C04B 35/63 | (2006.01) |

(52) U.S. Cl.
CPC ............ *B01D 53/48* (2013.01); *B01J 21/16* (2013.01); *B01J 35/002* (2013.01); *B01J 37/0009* (2013.01); *B01J 37/0018* (2013.01); *B01J 37/04* (2013.01); *B01J 37/088* (2013.01); *C01B 3/16* (2013.01); *C04B 35/45* (2013.01); *C04B 35/632* (2013.01); *C04B 35/6303* (2013.01); *C07C 29/154* (2013.01); *C10G 25/003* (2013.01); *C10L 3/103* (2013.01); B01D 2253/112 (2013.01); B01D 2253/1124 (2013.01); B01D 2257/30 (2013.01); B01D 2257/304 (2013.01); B01D 2257/502 (2013.01); B01D 2257/553 (2013.01); B01D 2257/602 (2013.01); B01D 2258/05 (2013.01); C01B 2203/0283 (2013.01); C01B 2203/061 (2013.01); C01B 2203/1076 (2013.01); C04B 2235/3217 (2013.01); C04B 2235/349 (2013.01); C04B 2235/3418 (2013.01); C04B 2235/442 (2013.01); C04B 2235/5436 (2013.01); C04B 2235/5472 (2013.01); C04B 2235/6021 (2013.01); C10G 2300/202 (2013.01); C10G 2300/207 (2013.01); C10L 2290/542 (2013.01)

(56) References Cited

U.S. PATENT DOCUMENTS

| | | | |
|---|---|---|---|
| 4,582,819 A | | 4/1986 | Miller |
| 5,850,047 A | * | 12/1998 | Tani .......... B22F 9/24 |
| | | | 75/246 |
| 5,853,681 A | * | 12/1998 | Denny .......... B01D 15/00 |
| | | | 423/225 |
| 7,411,080 B2 | * | 8/2008 | Zhao .......... C01G 3/00 |
| | | | 556/114 |
| 7,517,382 B2 | * | 4/2009 | Zhao .......... B22F 9/24 |
| | | | 75/373 |
| 7,566,357 B2 | * | 7/2009 | Zhao .......... B22F 9/24 |
| | | | 75/351 |
| 9,623,363 B2 | | 4/2017 | Girard |
| 9,908,084 B2 | * | 3/2018 | Fish .......... B01J 20/2803 |
| 10,343,137 B2 | * | 7/2019 | Evans .......... B01J 20/08 |
| 2007/0264152 A1 | * | 11/2007 | Zhao .......... B22F 3/1134 |
| | | | 420/591 |
| 2008/0064883 A1 | | 3/2008 | Schlitter |
| 2009/0162410 A1 | * | 6/2009 | Zhang .......... A01N 43/42 |
| | | | 424/409 |
| 2011/0206753 A1 | * | 8/2011 | Karpov .......... C01G 3/00 |
| | | | 424/405 |

OTHER PUBLICATIONS

Zhong Chun Chen et al: Effect of particle packing on extrusion behavior of pastes; Journal of Materials Science Nov. 2000, vol. 35, Issue 21, pp. 5301-5307 (Abstract).

* cited by examiner

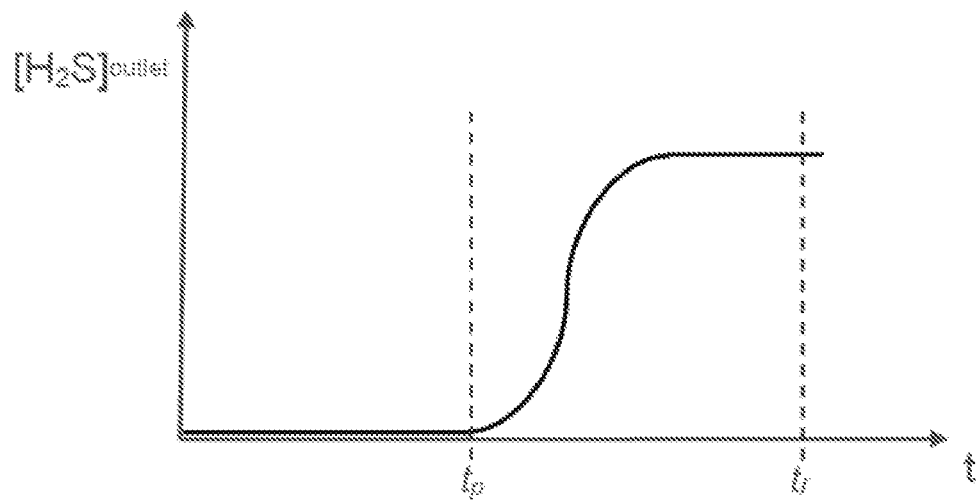

METHOD FOR PREPARING SOLIDS FROM A MIXTURE OF AT LEAST TWO MALACHITE POWDERS

FIELD OF THE INVENTION

The invention relates to a method for the preparation of solids based on copper compounds, as well as to the use of said solids for, inter alia, the removal of sulphur compounds from gaseous or liquid feedstocks, such as natural gases, biogas, synthesis gases, gases containing carbon dioxide $CO_2$, or liquid hydrocarbons.

The solids prepared according to the invention may also be used for the removal of carbon monoxide CO, compounds containing mercury, or compounds containing arsenic in gas or liquid feedstocks, as well as for the catalysis of the Dussan reaction (water-gas shift reaction).

PRIOR ART

Copper compounds are known from the prior art for their ability to react with sulphur compounds. The use of copper hydroxycarbonate as an active phase is of particular interest because the reaction with $H_2S$ seems to be particularly fast.

Many documents address desulphurisation in the presence of copper oxide.

U.S. Pat. No. 7,837,964 describes a desulphurisation material that may comprise up to 99.8 wt. % of copper oxide. The material is prepared by precipitation.

U.S. Pat. No. 4,582,819 describes a method for the desulphurisation of liquid hydrocarbons using solids prepared from copper hydroxycarbonate and alumina. The precursors are not peptised. The solid is thermally-treated, which partially degrades the copper hydroxycarbonate in order to obtain CuO, at a temperature above 260° C.

US 2013/047850 describes a method for the purification of synthesis gas ($H_2$, CO) using CuO-based solids, developed according to a method which makes it possible to prevent or mitigate the reduction of CuO during the industrial implementation of synthesis gas. For this purpose, the solids are prepared from copper hydroxycarbonate and a halogenated additive, for example NaCl, and a calcination step at a temperature of between 280 and 500° C. in order to completely decompose the copper carbonate into CuO.

Documents U.S. Pat. No. 6,007,706 and EP 243052 describe the removal of sulphur compounds by using a solid comprising at least 70 wt. % of a copper compound (carbonate or oxides or other).

However, none of said documents addresses the problem of the mechanical strength of the prepared materials.

The document FR 2940967 describes the preparation of a ZnO-based solid and the use thereof for the desulphurisation of liquid or gaseous feedstocks, said solid having excellent mechanical strength and an increased storage capacity. The preparation method comprises the steps of mixing ZnO powders, peptisation and calcination. According to said document, the basic peptisation of ZnO allows for a partial dissolution of ZnO in a basic medium, which results in a reduction of the size of the particles, a densified solid through better dispersion and therefore an increase in the mechanical strength.

However, malachite, which has the composition $Cu_2(OH)_2 CO_3$, is a basic compound which is not soluble in a basic medium, but is soluble in an acidic medium. Therefore, basic peptisation does not have a solubilisation effect which could lead to a decrease in particle sizes and, ultimately, to an improvement in the mechanical strength as described in FR 2940967.

Document WO 95/24962 describes capture masses containing at least 75 wt. % of copper carbonate, hydroxycarbonate or hydroxide. The text also relates to obtaining solids having a loading density of at least 0.9 kg/l, or even 1.2 kg/l, in order to improve the volume capture capacity of the solids (i.e. the amount of sulphur captured relative to the volume of the solid and not to the mass thereof). Said document indicates that the drying/calcination temperature should not exceed 150° C., or even 115° C., in order not to decompose the copper compounds used. This makes it possible to count the $CO_2$ and/or the water contained in the solids in the form of carbonate and hydroxide which thus contribute to the increase in density. Above 150° C., the decomposition of copper carbonate, hydroxycarbonate or hydroxide results in a decrease in the loading density of the solids. Moreover, said document does not describe a peptisation step.

However, solids prepared uniquely from copper hydroxycarbonate described in the prior art have particularly low mechanical strength properties, even after being thermally-treated, which makes them difficult to use, having, in particular, problems with attrition and the production of fine particles.

The applicant has discovered a method for preparing solids from copper hydroxycarbonate which have increased mechanical strength properties and effective sulphur capture capacities greater than those of the solids of the prior art.

BRIEF DESCRIPTION OF THE INVENTION

The invention relates to a method for preparing a solid, comprising the steps of:
a) mixing a set of compounds comprising at least two $Cu_2(OH)_2CO_3$ powders with different particle sizes and at least one binder;
b) contacting the mixture of step a) with an aqueous solution and kneading the paste thus obtained;
c) extruding the paste kneaded in step b) at a pressure of between 3 and 25 MPa;
d) calcinating the extrudates at a temperature of between 140° C. and 500° C. and for a duration of between 10 minutes and 6 hours under a gaseous flow comprising oxygen.

As well as very good mechanical strength, the obtained adsorbents have an optimised density and porosity, making it possible to maximise the useful mass capacity thereof while reducing the dispersion front during the capturing of the sulphur.

DETAILED DESCRIPTION OF THE INVENTION

In the rest of the description, the term prepared solid according to the invention means, without limitation, an adsorbent as well as a catalyst or capture mass depending on the use of said solid.

In the rest of the description, the terms malachite, copper hydroxycarbonate and $Cu_2(OH)_2CO_3$ are used without distinction.

Loss on ignition (LOI) of the solid is understood to be the loss of weight in wt. % of a sample of solid submitted to calcination at 550° C. for 2 hours.

Powder is understood to be a set of particles.

In the rest of the description, the size distribution of a powder or of particles is measured by granulometry by laser diffraction, based on the Mie scattering theory (G. B. J. de Boer, C. de Weerd, D. Thoenes, H. W. J. Goossens, Part. Charact. 4 (1987) 14-19). The distribution of the particle size of the said powder or said particles is represented by the median diameter ($D_{50}$), defined as being the diameter of the equivalent sphere such that 50 vol % of the said particles or the constituent particles of the said powder is smaller than the said diameter.

In the following, specific surface area can be understood as the BET specific surface area determined by the adsorption of nitrogen conforming to the ASTM D 3663-78 standard established from the BRUNAUER-EMMETT-TELLER method described in "The Journal of American Society", 60, 309, (1938).

Step a) Mixing

According to the invention, the preparation method comprises a step a) of mixing of a set of compounds comprising at least two $Cu_2(OH)_2CO_3$ powders with different particle sizes and at least one binder.

The said set of compounds comprises at least two $Cu_2(OH)_2CO_3$ powders with different particle sizes and at least one binder.

In an advantageous manner, the said set of compounds comprises 0.1 to 99.9 wt. %, advantageously 2 to 99.9 wt. %, preferably 5 to 99.9 wt. %, very preferably 5 to 99 wt. %, preferably 5 to 90 wt. % and very preferably 5 to 85% wt. % of a first malachite powder, the $D_{50}$ of which is between 1 and 15 µm, preferably between 1 and 10 µm and very preferably between 4 and 9 µm, and 99.9 to 0.1 wt. %, advantageously 98 to 0.1 wt. %, preferably 95 to 0.1 wt. %, very preferably 95 to 1 wt. %, preferably 95 to 10 wt. % and very preferably 95 to 15 wt. % of a second malachite powder, the $D_{50}$ of which is between 25 and 100 µm, preferably between 25 and 80 µm, preferably between 30 and 50 µm, the weight percentage being expressed relatively to the total weight of the malachite powders. A bimodal distribution improves the mechanical strength of the final solid obtained.

Advantageoulsy, the weighted median diameter (called Dm) of said set of compounds is between 10 and 45 µm, preferably between 15 and 45 µm, the limit values being included. The weighted median diameter (called Dm) of said set of compounds is calculated with the formula:

$$Dm = \Sigma_1^n x_n(Pn) \times D_{50}(Pn)$$

Where $x_n(Pn)$ is the mass fraction of the malachite powder Pn in said set of compounds, $D_{50}(Pn)$ is the $D_{50}$ of the malachite powder Pn of said set of compounds.

In an advantageous manner, the said set of compounds is free from copper oxide CuO powder.

The set of compounds is advantageously mixed in dry manner in step a), i.e. without adding liquid. The said step a) may be implemented, for example, in an agitator or any other type of mixer. The step makes it possible to obtain a homogeneous mixture of the powdered constituents.

Sources of $Cu_2(OH)_2CO_3$

The $Cu_2(OH)_2CO_3$ powders come from any source known to the person skilled in the art.

Binders

The set of compounds mixed in step a) comprises at least one binder. The said binder makes it possible to form the said adsorbent while providing good mechanical strength. The said binder is advantageously in powder form.

Any binder well known to the person skilled in the art may be used. In particular, the said binder may be advantageously selected, for example, from clays, such as kaolinite type minerals, palygorskite type minerals, and smectite clay minerals, such as montmorillonite or bentonite. The said binder can also be selected from the group consisting of alumina, a precursor of alumina, which is preferably boehmite, silica and mixtures thereof. It is absolutely possible to combine the use of binders of different types, such as an "alumina" binder and a "clay" binder, or even two clays of different types. According to a preferred embodiment of preparing the solid according to the invention, the binder is a bentonite type clay.

The amount of binder used in the preparation method according to the invention is such that the said binder represents less than 50 wt. % of the prepared solid (expressed on the basis of total dry matter, i.e. after loss on ignition), and depends on the intended application.

Whether for copper compounds or binder(s), it is quite possible to mix several sources of each compound.

When the solid prepared according to the invention is used for desulphurisation of the liquid or gas feedstock, the binder content of the said solid is preferably between 15 wt. % and 25 wt. % (expressed as total dry matter, i.e. after loss on ignition).

Step b) Peptisation and Kneading

According to the invention, the method for preparing an adsorbent comprises a step b) of contacting the mixture of step a) with an aqueous solution and kneading the obtained paste.

This step that results in obtaining a paste, allows the constituents to be dispersed, i.e. copper hydroxycarbonate powders as well as the binder(s), and the constituents to be partially dissolved.

Under the action of the aqueous solution, the phenomena of dispersion and dissolution of the copper hydroxycarbonate particles and the binder particles occurring during kneading by contacting different constituents are preferred. Without wishing to be restrictive about any theory, it is, however, possible to hypothesise that a better dispersion of both copper hydroxycarbonate and binder particles would move towards improving the mechanical strength ultimately obtained by said preparation method.

The said aqueous solution advantageously contains an acid or base peptising agent.

The said acid peptising agent can be nitric acid, hydrochloric acid, or any other acid known to the person skilled in the art, for example an inorganic acid, such as hydrofluoric acid, hydrobromic acid, hydrochloric acid, nitric acid, nitrous acid, sulphonic acid, sulphuric acid, perchloric acid, or even an organic mono- or di-carboxylic acid, such as acetic acid, propionic acid or butanoic acid.

In a particular arrangement of the method according to the invention, the peptisation is brought about using an acid aqueous solution containing nitric acid. The ratio of $HNO_3$ mass/metal oxides mass is between 0.5 and 10 wt. %, preferably between 0.5 and 6%, and advantageously between 0.5 and 3%.

The metallic oxides mass is calculated as follows:

$$\text{oxides } masse = \frac{2 \cdot M_{CuO}}{M_{Cu_2(OH)_2CO_3}} \cdot m_{Cu_2(OH)_2CO_3}$$

Where $m_{Cu2(OH)2CO3}$ is the mass of the $Cu_2(OH)_2CO_3$ malachite introduced in step a), $M_{CuO}$ is the molar mass of CuO (=80 g/mol), $M_{Cu2(OH)2CO3}$ is the molar mass of $Cu_2(OH)_2CO_3$ malachite (=222 g/mol).

The said basic peptising agent can be an inorganic base such as sodium hydroxide, potassium hydroxide, aqueous ammonia, or else an organic base such as an amine or a quaternary ammonium compound, selected, for example, from alkyl-ethanol amines or alkyl-ethoxylated amines.

In a particular arrangement of the method according to the invention, peptisation is carried out by means of an aqueous solution containing a basic peptising agent, such as, preferably, a basic peptising agent selected from the group consisting of sodium hydroxide, potassium hydroxide, aqueous ammonia, tetraethylammonium hydroxide (TEAOH), ammonium carbonate and mixtures thereof. The ratio of the basic peptising agent mass/metal oxides mass is between 1 and 10 wt. %, preferably between 2 and 8%, and advantageously between 2 and 5%. The oxides mass is calculated as the previous equation.

In another particular arrangement of the method according to the invention, the peptisation is brought about using an aqueous solution without added acid or base in step b). It has been observed in a surprising way that peptisation with water without the addition of acid or base makes it possible to obtain a solid presenting improved adsorption performances, in particular sulphur compounds. In this particular arrangement, the aqueous solution of the said step b) is advantageously deionised water, for example with the help of an ion exchange resin.

The amount of the aqueous solution used is adjusted in order to obtain, from peptisation and regardless of the variant implemented, a paste which does not flow, but which is no longer dry in order to allow the extrusion in step c) in suitable pressure conditions well known to the person skilled in the art and depending on the used extrusion equipment.

The contacting of reagents ($Cu_2(OH)_2CO_3$, binder(s), aqueous solution) is carried out by kneading in batches or continuously.

For batch kneading, equipment such as for example agitators with Z arms, rollers or cams are known to the person skilled in the art, but any other kneading equipment can also be used.

It is conceivable, during the kneading in step b), to incorporate one or more extrusion additives, thus making it possible to improve the flow of the paste in the channel during extrusion. These additives, well known to the person skilled in the art, may be selected from mono-carboxylic aliphatic acids, alkylated aromatic compounds, sulphonic acid salts, fatty acids, polyvinylpyridine, polyvinylpyrrolidone, polyvinyl alcohol, cellulosic derivatives, for example.

These additivesare generally added with a content between 0.1 wt. % and 10 wt. %, preferably between 0.2 wt. % and 8 wt. %, of the total mass of the constituents introduced into the agitator.

The duration of kneading is generally between 5 and 60 minutes, preferably between 20 and 50 minutes. The rotation speed of the agitator arms is between 10 and 75 rotations/minute, preferably between 25 and 50 rotations/minute.

Step c) Extrusion

According to the invention, the method for preparing an adsorbent comprises a step c) of extruding the paste kneaded in step b) at a pressure of between 3 and 25 MPa.

The said step c) of extruding may be implemented in any type of extruder, for example in a piston, single-screw or twin-screw extruder. The geometry of the die, which gives its shape to the extrudates may be selected from the dies known to the person skilled in the art. These dies may, for example, be cylindrical, trefoil, quatrefoil, fluted or with slits.

The diameter of the dies is defined according to the diameter of the desired solid from the calcination step.

Step b) of contacting and kneading and step c) of extruding may advantageously be combined in the same equipment. In an example of this implementation, the kneaded paste may be directly extruded at the end of a continuous twin-screw agitator. In another example of this implementation, one or a plurality of batch agitators are connected to an extruder.

The extrudates obtained from step c) are advantageously dried at a temperature of between 70 and 160° C. for between 1 and 24 hours before being calcinated in step d). This drying may advantageously be carried out under air or more preferably under humid air. The benefit of drying is to gently remove a part of the present volatile compounds, as direct calcination of the solid may result in the appearance of microfractures. Drying under humid air makes it possible to evaporate the said volatile compounds more slowly than drying under air.

Step d) Calcination

According to the invention, the method for preparing an adsorbent comprises a step d) of calcinating the extrudates at a temperature of between 140° C. and 500° C. and for a duration between 10 minutes and 6 hours under a gaseous flow comprising oxygen.

The said step d) of calcinating is carried out under a gaseous flow comprising oxygen. The said gaseous flow may advantageously be air, or a gaseous mixture comprising an inert gas (for example nitrogen) and oxygen. The said gaseous flow preferably comprises at least 5 vol. %, preferably at least 10 vol. % oxygen. The said gaseous flow also advantageously comprises water, preferably up to 3 vol. % water.

The said step d) of calcinating is carried out a temperature of between 140° C. and 500° C., preferably between 200° C. and 500° C., preferably between 200° C. and 350° C., for a duration of between 10 minutes and 6 hours, preferably between 10 minutes and 4 hours, preferably between 10 minutes and 3 hours, very preferably between 10 minutes and 2 hours, and very preferably between 15 minutes and 1 hour.

The calcination step makes it possible in particular to convert a fraction of malachite into copper oxide.

From step d) of calcination, the extrudates have a diameter of between 1 and 10 mm, preferably between 1 and 5 mm, and very preferably between 1.5 and 3.5 mm.

The solid according to the invention, obtained by means of extrusion, has a shape similar to a cylindrical rod. If necessary, these rods may be introduced into equipment making it possible to round their surface, such as a bezel, or any other equipment that can be used for the spheronization thereof.

The mass percentage of oxides (content of CuO from the decomposition of the malachite) contained in the solid after the loss on ignition may be determined as follows:

$$\% \text{ oxides } \textit{massafter LOI} = \frac{\frac{2 \cdot M_{CuO}}{M_{Cu_2(OH)_2CO_3}} \cdot m_{Cu_2(OH)_2CO_3}}{m_{binder} + \frac{2 \cdot M_{CuO}}{M_{Cu_2(OH)_2CO_3}} \cdot m_{Cu_2(OH)_2CO_3}}$$

Where $m_{binder}$ is the mass of the binder introduced in step a), $m_{Cu_2(OH)_2CO_3}$ is the mass of the $Cu_2(OH)_2CO_3$ malachite introduced in step a), $M_{CuO}$ is the molar mass of CuO (=80 g/mol), $M_{Cu2(OH)2CO3}$ is the molar mass of $Cu_2(OH)_2CO_3$ malachite (=222 g/mol).

The solid prepared according to the invention comprises at least:
- 50 to 99 wt. %, preferably 60 to 95 wt. %, more preferably 75 to 85 wt. % equivalent in mass of CuO measured after loss on ignition at 550° C. for 2 hours, content determined according to the preceding equation.
- 1 to 50 wt. %, preferably 5 to 40 wt. %, more preferably 15 to 25 wt. % of a binder, the mass percentage being measured after loss on ignition.

These contents in wt. % are expressed relatively to the total mass of the solid prepared by means of the method according to the invention, and measured after decomposition of precursors at 550° C. for 2 hours.

Properties of the Solid Obtained By Means of the Method According to the Invention The mechanical properties are determined by the grain by grain crushing test (EGG) described by the ASTM D 6175-3 method. This consists of measuring the breaking strength of each particle of a representative sample comprising at least 50 particles. The result is weighted by the length of the extrudate. The EGG value is the average of the breaking strengths measured and reduced to the unit length of the extrudate (expressed in $daN \cdot mm^{-1}$) for all of the sample particles.

In the case of solids prepared according to the invention, the EGG value is greater than 0.7 $daN \cdot mm^{-1}$ (decanewtons per millimetre of length of the extrudate), preferably greater than 0.9 $daN \cdot mm^{-1}$, and regardless of the copper hydroxycarbonate content used.

Moreover, the obtained solids used as adsorbents have improved desulphurisation performances with respect to the treatment of gases and liquids containing sulphur compounds, in particular $H_2S$, mercaptans, COS and $CS_2$.

Surprisingly, solids prepared with the method according to the invention, from a specific blend of malachite powders, exhibit satisfactory mechanical strength, with costs of production and in particular with limited supply costs for the starting malachite powders that are limited and thus industrially acceptable.

Use of the Solid Obtained By Means of the Method According to the Invention

The invention also relates to the use of the solid prepared by means of the method according to the invention.

The solid prepared according to the invention may be used to purify gaseous feedstocks, such as, for example, gaseous hydrocarbons, such as natural gases, biogases, gases containing carbon dioxide $CO_2$, or synthesis gases, such as those used in cogeneration plants, in chemical synthesis units, such as methanol synthesis or Fischer-Tropsch synthesis units, or liquids, such as hydrocarbons used as feedstocks in catalytic reforming, isomerisation, or hydrogenation units.

The solid prepared according to the invention is advantageously used to purify any gaseous or liquid feedstock containing, inter alia, sulphur compounds, such as $H_2S$, COS and/or $CS_2$, and/or mercaptans, at a pressure of between 0.1 and 25 MPa, preferably between 0.1 and 15 MPa, and a temperature of between 0 and 450° C., preferably between 15 and 300° C., preferably between 15 and 250° C.

In particular, the solid prepared according to the invention may advantageously be used to purify the feedstock of a Fischer-Tropsch synthesis unit, by being used in a reactor operating at a pressure of between 0.1 and 15 MPa, preferably between 1.5 and 5.0 MPa, at a temperature of between 0 and 400° C., preferably between 0 and 220° C., preferably between 15 and 180° C.

The said solid prepared according to the invention may also be used in order to remove some heteroelements, such as phosphorus or compounds thereof, such as phosphine $PH_3$, and/or chlorine, in particular in the form of HCl, present in the liquid or gaseous effluents, preferably at a pressure of between 0.1 and 25 MPa, preferably between 1 and 15 MPa, and at a temperature of between 0 and 200° C.

The said solid prepared according to the invention may also be used in order to remove heavy metals, such as mercury, and/or arsenic or its compounds, such as arsine $AsH_3$, present in the liquid or gaseous effluents, preferably at a pressure of between 0.1 and 25 MPa, preferably between 1 and 15 MPa, and at a temperature of between 0 and 200° C.

Indeed, if the feedstock to be purified contains mercury in addition to sulphur compounds, the said solid prepared by means of the method according to the invention also makes it possible to remove the mercury present in the feedstock to be treated.

The solid prepared according to the invention may advantageously undergo a step of sulphurisation before the industrial use thereof in a method for capturing mercury if the feedstock to be treated does not contain sulphur compounds.

The solid prepared according to the invention may also be used in order to remove carbon monoxide CO present in the liquid or gaseous effluents, at a temperature of between 0 and 200° C. and at a pressure of between 0.1 and 25 MPa.

The solid prepared according to the invention is used by contacting the gaseous or liquid feedstock to be treated with the said solid in a reactor, which may be a fixed bed reactor, a radial flow reactor, or even a fluidised bed reactor.

The solid prepared according to the invention may also be reduced under a reducing atmosphere, such as a hydrogen flow, with a synthesis gas then used as a catalyst for Dussan or water-gas shift reactions, or as a catalyst for the synthesis of methanol from synthesis gas.

The typical usage conditions of the solid as a catalyst for the methanol synthesis reaction are a temperature of between 100 and 500° C., preferably between 150 and 300° C., even preferably between 220 and 280° C., and a pressure of between 0.1 and 25 MPa, preferably between 1 and 15 MPa, and even more preferably between 5 and 10 MPa.

The typical usage conditions of the solid as a catalyst for the Dussan reaction are a temperature of between 100 and 500° C., preferably between 150 and 300° C., even preferably between 180 and 250° C., and a pressure of between 0.1 and 25 MPa, preferably between 1 and 15 MPa, and even more preferably between 1.5 and 10 MPa.

DESCRIPTION OF THE DRAWING

FIG. 1 is a schematic representation of a breakthrough curve which can be obtained according to the protocol for measuring the impurity capture capacity by the solids, described below. In FIG. 1, $t_p$ is the breakthrough time and $t_f$ is the end of the breakthrough time.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 17/55.303, filed Jun. 13, 2017 are incorporated by reference herein.

EXAMPLES

Protocol for Measuring the Impurity Capture Capacity By the Solids Prepared

The impurity capture capacity of solids prepared by means of the method according to the invention is measured using a breakthrough test.

For the test to determine the $H_2S$ capture capacity, the test is carried out at a temperature of 50° C., at a pressure of 0.3 MPa, and with an hourly volume velocity (HVV) of 1530 $h^{-1}$. Hourly volume velocity can be understood as the ratio of the volumetric flow rate of gas measured at 0° C. and 1 atm to the volume of the solid tested. The gas used for the test contains 0.9 vol. % of $H_2S$ in nitrogen. The $H_2S$ content present in the gas leaving the reactor containing the solid is determined by gas chromatography.

The species i capture capacity by the solid prepared by means of the method according to the invention is determined by carrying out a material balance. The species i capture capacity, as defined within the present invention, corresponds to the amount of the species i accumulated by the solid before breakthrough (i.e. at the time $t_p$ indicated in FIG. 1, which schematically represents a breakthrough curve), this being calculated by means of the following equation:

$$q_i = M_i D_i^E \int_0^{t_p} \left(1 - \frac{C_i^S}{C_i^E}\right) dt$$

Where:
$q_i$: is the mass of the species i captured by the solid (in g),
$D_i^E$: is the inflow of the species i (in mol·min$^{-1}$),
$M_i$: is the molar mass of the species i (in g·mol$^{-1}$),
$C_i^E$: is the species i content of the inflow gas,
$C_i^S$: is the species i content at the reactor outlet,
$t_p$: is the time needed for the breakthrough of the species i (in minutes) as shown in FIG. 1.

In FIG. 1, $t_p$ is the breakthrough time and $t_f$ is the end of the breakthrough time.

The species i capture capacity of the solid tested is provided by the equation:

$$C_i = \frac{q_i}{m}$$

where m is the mass of adsorbent used during the test.

Example 1

According to the Prior Art

In example 1, the reference solids A1, A2, A3, A4 and A5 are prepared according to the following procedure:

a) mixing a set of compounds comprising a $Cu_2(OH)_2CO_3$ powder and a binder;
b) contacting the mixture of step a) with an aqueous solution (peptisation) and kneading the paste thus obtained in a Z-arm mixer for 30 minutes with an arm rotation speed of 25 rotations·minutes$^{-1}$;
c) extruding the paste kneaded in step b) by means of a piston extruder, with a diameter of 3 mm and a length of 5 to 10 mm at a variable pressure depending on the solids;
d) calcinating the extrudates at a variable temperature depending on the solids, carried out for 1 hour, under an air flow.

In step a) a malachite powder P1 is used, the $D_{50}$ of which is 48 μm.

A bentonite clay was used as a binder.

The CuO contents or mass percentage of oxides (CuO from the decomposition of the malachite) after loss on ignition (550° C. for 2 hours) are 80 wt. % for solids A1, A2, A3 and A4, and 60 wt. % for solid A5 (with the bentonite binder as the complement). These contents are determined according to the following equation:

$$\% \text{ weight CuO after } LOI = \frac{\frac{2 \cdot M_{CuO}}{M_{Cu_2(OH)_2CO_3}} \cdot m_{Cu_2(OH)_2CO_3}}{m_{binder} + \frac{2 \cdot M_{CuO}}{M_{Cu_2(OH)_2CO_3}} \cdot m_{Cu_2(OH)_2CO_3}}$$

Where $m_{binder}$ is the mass of the binder introduced in step a), $m_{Cu2(OH)2CO3}$ is the mass of the $Cu_2(OH)_2CO_3$ malachite introduced in step a), $M_{CuO}$ is the molar mass of CuO (=80 g/mol), $M_{Cu2(OH)2CO3}$ is the molar mass of $Cu_2(OH)_2CO_3$ malachite (=222 g/mol).

For solids A1, A2 and A3, the amount of NaOH base is 4% by weight relatively to the total amount of $Cu_2(OH)_2CO_3$ introduced.

For solids A4 and A5, deionised water is used as the aqueous solution for step b) of kneading.

During the extrusion, the pressure varies between 50 and 150 bar depending on the formulation used.

The formulations of solids A1, A2, A3, A4 and A5 are given in Table 1.

TABLE 1

| Designation | % oxides after LOI | Binder | Peptisation | Calcination temperature (° C.)/duration (h) | Test for capturing $H_2S$: Sulphur captured at tp (g S/g solid) | EGG (daN · mm$^{-1}$) |
|---|---|---|---|---|---|---|
| Solid A1 | 80% | Bentonite | 4% NaOH | 140° C./1 h | 0.22 | 0.5 |
| Solid A2 | 80% | Bentonite | 4% NaOH | 250° C./1 h | 0.25 | 0.5 |

TABLE 1-continued

| Designation | % oxides after LOI | Binder | Peptisation | Calcination temperature (° C.)/duration (h) | Test for capturing H$_2$S: Sulphur captured at tp (g S/g solid) | EGG (daN · mm$^{-1}$) |
|---|---|---|---|---|---|---|
| Solid A3 | 80% | Bentonite | 4% NaOH | 350° C./1 h | 0.24 | 0.5 |
| Solid A4 | 80% | Bentonite | water | 250° C./1 h | 0.26 | 0.3 |
| Solid A5 | 60% | Bentonite | water | 250° C./1 h | 0.16 | 0.6 |

The mechanical strength of the extrudates is determined by a grain by grain crushing test (EGG) as previously described.

The mechanical strength of solids A1 to A5 is too low taking into consideration the constraints associated with an industrial use. The EGG values measured are indeed lower than 0.7 daN·mm$^{-1}$, whatever the calcination temperature and the presence or lack of sodium hydroxide during peptisation when a single powder having a single particle size distribution is used.

The increase in binder content and the decrease in malachite content in solid A5 results in a slight increase in mechanical strength which is nevertheless insufficient, to the detriment of the sulphur capture capacity thereof. In this latter case, the sulphur capacity becomes weak compared to that of the solids according to the invention.

Example 2

According to the Invention

In example 2, the solids referenced as B1 to B4 according to the invention are prepared by kneading and extruding according to the following procedure:
a) mixing a set of compounds comprising two Cu$_2$(OH)$_2$CO$_3$ powders and a binder;
b) contacting the mixture of step a) with an aqueous solution (peptisation) and kneading the paste thus obtained in a Z-arm mixer for 30 minutes with an arm rotation speed of 25 rotations·minutes$^{-1}$;
c) extruding the paste kneaded in step b) by means of a piston extruder, with a diameter of 3 mm and a length of 5 to 10 mm at a variable pressure depending on the solids;
d) calcinating the extrudates at a variable temperature depending on the examples, carried out for 1 hour, under air flow.

In step a) two malachite powders P1 and P2, having different particle sizes, are used. The D$_{50}$ of powder P1 is 48 μm, and the D$_{50}$ of powder P2 is 5 μm.

The relative amounts of the introduced malachite P1 and P2 are expressed using the ratios % P1 and % P2 defined by:

$$\% \text{ malachite } P1 = \frac{m_{P1}}{m_{P1} + m_{P2}}$$

$$\% \text{ malachite } P2 = \frac{m_{P2}}{m_{P1} + m_{P2}}$$

Where m$_{P1}$ is the mass of malachite P1 introduced in step a), and m$_{P2}$ is the mass of malachite P2 introduced in step a), A bentonite clay was used as a binder.

The content of CuO from the decomposition of malachite after loss on ignition (550° C. for 2 hours) is 80 wt. % for solids B1 to B4. This content is determined according to the following equation:

$$\% \text{ weight CuO after } LOI = \frac{\frac{2 \cdot M_{CuO}}{M_{Cu_2(OH)_2CO_3}} \cdot m_{Cu_2(OH)_2CO_3}}{m_{binder} + \frac{2 \cdot M_{CuO}}{M_{Cu_2(OH)_2CO_3}} \cdot m_{Cu_2(OH)_2CO_3}}$$

Where m$_{binder}$ is the mass of the binder introduced in step a), m$_{Cu2(OH)2CO3}$ is the mass of the Cu$_2$(OH)$_2$CO$_3$ malachite powders introduced in step a) m$_{Cu2(OH)2CO3}$=m$_{P1}$+m$_{P2}$), M$_{CuO}$ is the molar mass of CuO (=80 g/mol), M$_{Cu2(OH)2CO3}$ is the molar mass of Cu$_2$(OH)$_2$CO$_3$ malachite (=222 g/mol).

For solids B1, B2, B3, B4, B5 and B6, deionised water is used as the aqueous solution for step b) of kneading.

For solid B7, the amount of NaOH base is 4% by weight relatively to the total amount of introduced Cu$_2$(OH)$_2$CO$_3$.

During the extrusion, the pressure varies between 50 and 200 bar depending on the used formulation.

The formulations of the solids are given in Table 2.

TABLE 2

| Designation | % P1 of total malachite | % P2 of total malachite | Dm (μm) | % oxides after LOI | Binder | Peptisation | Calcination temperature (° C.)/duration (h) | Test for capturing H$_2$S: Sulphur captured at tp (g S/g solid) | EGG (daN · mm$^{-1}$) |
|---|---|---|---|---|---|---|---|---|---|
| Solid B1 | 87.5% | 12.5% | 42.6 | 80% | Bentonite | water | 250° C./1 h | 0.25 | 0.8 |
| Solid B2 | 75% | 25% | 37.3 | 80% | Bentonite | water | 250° C./1 h | 0.24 | 1.2 |
| Solid B3 | 50% | 50% | 26.5 | 80% | Bentonite | water | 250° C./1 h | 0.26 | 1.2 |
| Solid B4 | 25% | 75% | 15.8 | 80% | Bentonite | water | 250° C./1 h | 0.25 | 1.2 |
| Solid B5 | 87.5% | 12.5% | 42.6 | 80% | Bentonite | water | 140° C./1 h | 0.23 | 0.7 |

TABLE 2-continued

| Designation | % P1 of total malachite | % P2 of total malachite | Dm (μm) | % oxides after LOI | Binder | Peptisation | Calcination temperature (° C.)/duration (h) | Test for capturing $H_2S$: Sulphur captured at tp (g S/g solid) | EGG (daN · mm$^{-1}$) |
|---|---|---|---|---|---|---|---|---|---|
| Solid B6 | 87.5% | 12.5% | 42.6 | 80% | Bentonite | water | 350° C./1 h | 0.22 | 0.7 |
| Solid B7 | 87.5% | 12.5% | 42.6 | 80% | Bentonite | 4% NaOH | 250° C./1 h | 0.20 | 0.9 |

The use of two $Cu_2(OH)_2CO_3$ powders of different particle sizes in the preparation method according to the invention, with Dm for starting powders blend between 15 and 45 μm, makes it possible to obtain solids having satisfactory mechanical properties (EGG greater than 0.7 daN·mm$^{-1}$).

Furthermore, the solids have satisfactory sulphurisation capacities, greater than 0.15 grams of sulphur/gram of solid in the test conditions described in the document.

Example 3

Comparative Example

In example 3, the solids C1 and C2 are prepared by kneading and extruding according to the operating method of Example 2.

The two malachite powders P1 and P2 used to prepare the solid C have the following particle sizes: $D_{50}$ for powder P1 is 50 μm and $D_{50}$ for powder P1 is 50 μm.

Solid C is tested with the same conditions as those used for Example 2 tests.

Table 3 presents the formulation of solids C and the obtained results.

TABLE 3

| Designation | % P1 of total malachite | % P2 of total malachite | Dm (μm) | % oxides after LOI | Binder | Peptisation | Calcination temperature (° C.)/duration (h) | Test for capturing $H_2S$: Sulphur captured at tp (g S/g solid) | EGG (daN · mm$^{-1}$) |
|---|---|---|---|---|---|---|---|---|---|
| Solid C1 | 93.75% | 6.25% | 47.5 | 80% | Bentonite | water | 250° C./1 h | 0.25 | 0.6 |
| Solid C2 | 96.87 | 3.13 | 48.7 | 80% | Bentonite | water | 250° C./1 h | 0.25 | 0.6 |

The EGG values measured for the solids C1 and C2 are lower than 0.7 daN·mm$^{-1}$. The mechanical strength of solids C1 and C2 is too low taking into consideration the constraints associated with an industrial use.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. Method for preparing a solid comprising the steps of:
   a) mixing a set of compounds comprising at least two $Cu_2(OH)_2CO_3$ powders with different particle sizes and at least one binder;
   b) contacting the mixture of step a) with an aqueous solution and kneading the paste thus obtained;
   c) extruding the paste kneaded in step b) at a pressure of between 3 and 25 MPa;
   d) calcinating the extrudates at a temperature of between 140° C. and 500° C. and for a duration of between 10 minutes and 6 hours under a gaseous flow comprising oxygen.

2. Method according to claim 1, wherein the said set of compounds comprises 0.1 to 99.9 wt. % of a first malachite powder, the $D_{50}$ of which is between 1 and 15 μm and 99.9 to 0.1 wt. % of a second malachite powder, the $D_{50}$ of which is between 25 and 100 μm, the weight percentage being expressed relatively to the total weight of the malachite powders.

3. Method according to claim 1, wherein the said set of compounds is dry-mixed in step a), i.e. without adding liquid.

4. Method according to claim 1, wherein the said binder is selected from clays, or selected from the group consisting of alumina, a precursor of alumina, silica and mixtures thereof.

5. Method according to claim 1, wherein the amount of binder used in the preparation method is such that the said binder represents less than 50 wt. % of the prepared solid.

6. Method according to claim 1, wherein the said aqueous solution of the said step b) contains an acidic or basic peptizing agent.

7. Method according to claim 6, wherein the said aqueous solution of the said step b) contains nitric acid, the ratio of $HNO_3$ mass/metal oxides mass being between 0.5 and 10 wt. %.

8. Method according to claim 6, wherein the said basic peptising agent is selected from the group consisting of sodium hydroxide, potassium hydroxide, ammonia, tetraethylammonium hydroxide (TEAOH), ammonium carbonate and mixtures thereof, the ratio of the basic peptizing agent mass/metal oxides mass being between 1 and 10 wt. %.

9. Method according to claim 1, wherein the aqueous solution of the said step b) is an aqueous solution with no added acid or base.

10. Method according to claim 1, wherein the extrudates obtained from step c) are dried at a temperature of between 70 and 160° C. for a duration of between 1 and 24 hours before being calcined in step d).

11. Method according to claim 1, wherein step d) of calcination is carried out at a temperature of between 200° C. and 500° C.

* * * * *